United States Patent [19]

Hamprecht et al.

[11] 4,316,014
[45] Feb. 16, 1982

[54] 5,6-DIHYDRO-1,2,4,6-THIATRIAZIN-5-ONE-1,1-DIOXIDES

[75] Inventors: Gerhard Hamprecht, Weinheim; Rolf-Dieter Acker, Leimen; Bruno Wuerzer, Otterstadt, all of Fed. Rep. of Germany

[73] Assignee: BASF Aktiengesellschaft, Fed. Rep. of Germany

[21] Appl. No.: 166,856

[22] Filed: Jul. 8, 1980

[30] Foreign Application Priority Data

Aug. 22, 1979 [DE] Fed. Rep. of Germany ........ 2933889

[51] Int. Cl.³ .......................................... C07D 285/00
[52] U.S. Cl. ........................................ 544/7
[58] Field of Search .............................. 544/7

[56] References Cited

FOREIGN PATENT DOCUMENTS 925101 4/1973 Canada .
1946262 3/1971 Fed. Rep. of Germany .
2026625 12/1971 Fed. Rep. of Germany .
2508832 9/1975 Fed. Rep. of Germany .

Primary Examiner—John M. Ford
Attorney, Agent, or Firm—Keil & Witherspoon

[57] ABSTRACT

5,6-Dihydro-1,2,4,6-thiatriazin-5-one-1,1-dioxides of the formula

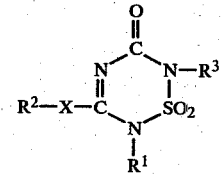

where
$R^1$ is hydrogen, a metal atom or an unsubstituted or substituted ammonium radical,
$R^2$ is a saturated or unsaturated straight-chain aliphatic radical of up to 10 carbon atoms, a cycloaliphatic radical or 3 to 7 carbon atoms, a branched saturated or unsaturated aliphatic radical of 3 to 10 carbon atoms, a halogen-, alkoxy- or alkylmercapto-substituted aliphatic radical of 2 to 10 carbon atoms tetrahydrofuryl substituted methyl, a cycloalkoxy-substituted aliphatic radical of 4 to 10 carbon atoms, unsubstituted or halogen-substituted benzyl or phenyl, halophenyl, or alkylphenyl of a total of up to 10 carbon atoms,
$R^3$ is hydrogen, a straight-chain aliphatic radical of up to 10 carbon atoms, a cycloaliphatic radical of 3 to 7 carbon atoms, a branched aliphatic radical of 3 to 10 carbon atoms, haloalkyl, or alkoxyalkyl of 2 to 10 carbon atoms and
X is oxygen and may also be sulfur if $R^2$ is unsubstituted or halogen-substituted benzyl, processes for their preparation, and herbicides containing the above compounds.

2 Claims, No Drawings

5,6-DIHYDRO-1,2,4,6-THIATRIAZIN-5-ONE-1,1-DIOXIDES

The present invention relates to novel 5,6-dihydro-1,2,4,6-thiatriazin-5-one-1,1-dioxides, processes for their preparation, herbicides which contain these compounds as active ingredients, and processes for controlling undesired plant growth by means of these compounds.

German Laid-Open Application DOS 1,946,262 discloses substituted 5,6-dihydro-1,2,4,6-thiatriazin-5-one-1,1-dioxides as active ingredients for plant treatment agents. The herbicidal activity of these compounds is disclosed in German Laid-Open Application DOS No. 2,508,832.

We have found that 5,6-dihydro-1,2,4,6-thiatriazin-5-one-1,1-dioxide derivatives of the formula

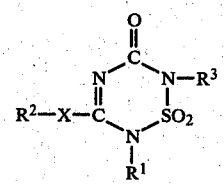

where
$R^1$ is hydrogen, a metal atom or an unsubstituted or substituted ammonium radical,
$R^2$ is a saturated or unsaturated straight-chain aliphatic radical of up to 10 carbon atoms, a cycloaliphatic radical of 3 to 7 carbon atoms, a branched saturated or unsaturated aliphatic radical of 3 to 10 carbon atoms, a halogen-, alkoxy- or alkylmercapto-substituted aliphatic radical of 2 to 10 carbon atoms, tetrahydrofuryl substituted methyl, a cycloalkoxy-substituted aliphatic radical of 4 to 10 carbon atoms, unsubstituted or halogen-substituted benzyl or unsubstituted, halogen-substituted or alkyl-substituted phenyl of up to 10 carbon atoms,
$R^3$ is hydrogen, a straight-chain aliphatic radical of up to 10 carbon atoms, a cycloaliphatic radical of 3 to 7 carbon atoms, a branched aliphatic radical of 3 to 10 carbon atoms or haloalkyl or alkoxyalkyl of 2 to 10 carbon atoms and
X is oxygen and may also be sulfur if $R^2$ is unsubstituted or halogen-substituted benzyl, on the one hand exhibit surprising selective herbicidal properties when used in certain crops, and, on the other hand, exhibit a substantial herbicidal action both on annual weeds and on perennial weeds which are otherwise difficult to control.

In formula I, $R^1$ is, for example, sodium, potassium, ammonium, dimethylammonium, tridecylammonium, trimethylammonium, triethanolammonium, N-methyl-N,N-diethanolammonium, diisopropylammonium or polyoxyethylated dimethylammonium.

In formula I, $R^2$ and $R^3$ are, for example, methyl, ethyl, propyl, isopropyl, cyclopropyl, butyl, isobutyl, sec.-butyl, tert.-butyl, pentyl, cyclopentyl, hexyl, cyclohexyl, 3-pentyl, 1,2-dimethylpropyl, 1,3-dimethylbutyl, 2-chloroethyl, 2-chloropropyl, 3-chloropropyl, 2-chloroisopropyl, 1-chloromethylpropyl, 1-ethyl-2-methylpropyl, 1,2,2-trimethylpropyl, 1,2-dimethylhexyl, 1-cyclohexylethyl, 2-chlorobut-3-yl, 2-chloro-2-methylpropyl, 2-fluorobut-3-yl, 2-fluoro-2-methylpropyl, 2-fluoroisopropyl, tert.-amyl, chloro-tert.-butyl, 2,2,2-trifluoroethyl, methoxyethyl, ethoxyethyl, 3-methoxypropyl, methoxyisopropyl, 3-methoxybutyl, 1-methoxybut-2-yl, ethoxy-tert.-butyl, methoxy-tert.-butyl, 2-methoxy-butyl and 4-methoxy-butyl.

In addition, $R^2$ may be, for example, allyl, methallyl, crotyl, 2-ethyl-hex-2-en-1-yl, hex-5-en-1-yl, 2-methylbut-2-en-1-yl, 2-methyl-but-1-en-3-yl, but-1-yn-3-yl, but-2-yn-1-yl, but-1-en-3-yl, propargyl, 2-methyl-but-1-en-4-yl, 2-methyl-but-2-en-4-yl, 3-methyl-but-1-en-3-yl, methylmercapto-ethyl, ethylmercaptoethyl, 3-methylmercapto-propyl, 3-methylmercapto-butyl, 1-methylmercapto-but-2-yl, methylmercapto-tert.-butyl, 2-methylmercapto-butyl, cyclohexoxy-ethyl, benzyl, 2,6-dichlorobenzyl, 2-chloro-6-fluorobenzyl, 2,6-difluorobenzyl, phenyl, 4-chlorophenyl, 2,4-dichlorophenyl, 4-isopropylphenyl and 4-tert.-butylphenyl.

For the purposes of the invention, halogen is fluorine, chlorine, bromine or iodine.

We have found, further, that 1,2,4,6-thiatriazin-5-one-1,1-dioxide derivatives of the formula I, where X is oxygen, are obtained when an N-carboalkoxy-O-alkylisourea of the formula

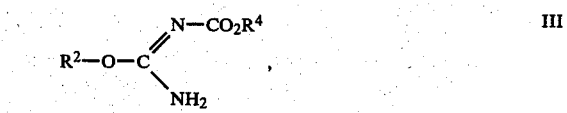

where $R^2$ has the above meanings and $R^4$ is alkyl of 1 to 4 carbon atoms, is reacted with an aminosulfonyl halide of the formula

where $R^3$ has the above meanings and Y is fluorine or chlorine, in the presence or absence of an acid acceptor and of an inert organic solvent, at from $-20°$ to $+80°$ C., under atmospheric or superatmospheric pressure, continuously or batchwise, to give a sulfonediamide of the formula

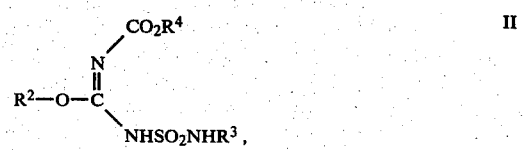

where $R^2$, $R^3$ and $R^4$ have the above meanings, and this compound is cyclized, with or without prior isolation, in the presence of a basic compound at from 0° to 100° C.

N-Carboalkoxy-O-alkylisoureas of the formula III are known or can be prepared by conventional methods.

If N-carbomethoxy-O-methylisourea and isopropylaminosulfonyl chloride are used as starting materials, the course of the reaction can be represented by the following equations:

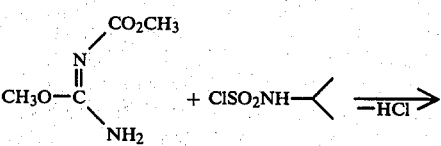

-continued

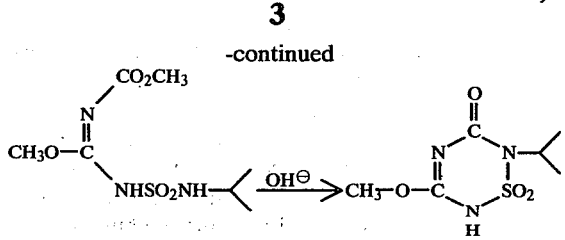

Organic solvents which may be used are those which are inert under the reaction conditions. Examples of suitable solvents are halohydrocarbons, especially chlorohydrocarbons, eg. tetrachloroethylene, 1,1,2,2- and 1,1,1,2-tetrachloroethane, dichloropropane, methylene chloride, dichlorobutane, chloroform, chloronaphthalene, dichloronaphthalene, carbon tetrachloride, 1,1,1- and 1,1,2-trichloroethane, trichloroethylene, pentachloroethane, o-, m- and p-difluorobenzene, 1,2-dichloroethane, 1,1-dichloroethane, 1,2-cis-dichloroethylene, chlorobenzene, fluorobenzene, bromobenzene, iodobenzene, o-, p- and m-dichlorobenzene, o-, p- and m-dibromobenzene, o-, m- and p-chlorotoluene and 1,2,4-trichlorobenzene; ethers, eg. ethyl propyl ether, methyl tert.-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane, thioanisole and $\beta,\beta'$-dichlorodiethyl ether; nitrohydrocarbons, eg. nitromethane, nitroethane, nitrobenzene, o-, m- and p-chloronitrobenzene and o-nitrotoluene; nitriles, eg. acetonitrile, butyronitrile, isobutyronitrile, benzonitrile and m-chlorobenzonitrile; aliphatic and cycloaliphatic hydrocarbons, eg. heptane, pinane, nonane, o-, m- and p-cymene, gasoline fractions with boiling points within the range from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane and octane; esters, eg. ethyl acetate, ethyl acetoacetate and isobutyl acetate; amides, eg. formamide, methylformamide and dimethylformamide; ketones, eg. acetone and methyl ethyl ketone; and mixtures of the above. The solvent is advantageously used in an amount of from 100 to 2,000% by weight, preferably from 200 to 700% by weight, based on starting material III.

All conventional acid-binding agents may be used as acid acceptors, but tertiary amines, alkaline earth metal compounds, ammonium compounds and alkali metal compounds, as well as mixtures of these, are preferred. However, zinc compounds may also be used. Examples of suitable basic compounds are potassium hydroxide, sodium hydroxide, potassium carbonate, sodium carbonate, lithium hydroxide, lithium carbonate, sodium bicarbonate, potassium bicarbonate, calcium hydroxide, calcium oxide, barium oxide, magnesium hydroxide, magnesium oxide, barium hydroxide, calcium carbonate, magnesium carbonate, magnesium bicarbonate, magnesium acetate, zinc hydroxide, zinc oxide, zinc carbonate, zinc bicarbonate, zinc acetate, sodium formate, sodium acetate, trimethylamine, triethylamine, tripropylamine, triisopropylamine, tributylamine, triisobutylamine, tri-sec.-butylamine, tri-tert.-butylamine, tribenzylamine, tricyclohexylamine, triamylamine, trihexylamine, N,N-dimethylaniline, N,N-diethylaniline, N,N-dipropylaniline, N,N-dimethyltoluidine, N,N-diethyltoluidine, N,N-dipropyltoluidine, N,N-dimethyl-p-aminopyridine, N,N-diethyl-p-aminopyridine, N,N-dipropyl-p-aminopyridine, N-methylpyrrolidone, N-ethylpyrrolidone, N-methylpiperidine, N-ethylpiperidine, N-methylpyrrolidine, N-ethylpyrrolidine, N-methylimidazole, N-ethylimidazole, N-methylpyrrole, N-ethylpyrrole, N-methylmorpholine, N-ethylmorpholine, N-methylhexamethyleneimine, N-ethylhexamethyleneimine, pyridine, quinoline, $\alpha$-picoline, $\beta$-picoline, $\gamma$-picoline, isoquinoline, pyrimidine, acridine, N,N,N',N'-tetramethylethylenediamine, N,N,N',N'-tetraethylethylenediamine, quinoxaline, quinazoline, N-propyldiisopropylamine, N,N-dimethylcyclohexylamine, 2,6-lutidine, 2,4-lutidine, trifurfurylamine and triethylenediamine.

Examples of suitable cyclizing agents are the above inorganic acid-binding agents, and also, for example, sodium propionate, sodium butyrate, sodium isobutyrate, potassium formate, potassium acetate, potassium propionate, potassium butyrate, potassium isobutyrate, sodium methylate, sodium ethylate, sodium propylate, sodium isopropylate, sodium butylate, sodium isobutylate, sodium sec.-butylate, sodium tert.-butylate, sodium ethylene-glycolate, sodium 1,2-propylene-glycolate, sodium 1,3-propylene-glycolate, sodium diethyleneglycolate, sodium triethylene-glycolate, sodium 1,2-dipropylene-glycolate, potassium methylate, potassium ethylate, potassium n-propylate, potassium isopropylate, potassium n-butylate, potassium isobutylate, potassium sec.-butylate, potassium tert.-butylate, potassium ethylene-glycolate, potassium 1,2-propylene-glycolate, potassium 1,3-propylene-glycolate, potassium diethyleneglycolate, potassium triethylene-glycolate and potassium 1,2-dipropylene-glycolate.

The acid-binding agents are advantageously employed in equivalent amounts or in an excess of up to 20%, based on aminosulfonyl halide of the formula IV.

The cyclization is carried out in the presence of from 1 to 2.5 moles of basic cyclizing agent per mole of sulfonediamide of the formula II.

The starting materials of the formulae III and IV are employed in about the stoichiometric ratio, ie. the starting material of the formula IV may be present in up to 20% excess over the starting material of the formula III, or vice versa.

The process is advantageously carried out by running the aminosulfonyl halide of the formula IV and the equivalent amount of acid acceptor, via two separate feed lines, into an about equivalent amount of N-carboalkyl-O-alkylisourea of the formula III in an inert organic solvent, at from $-20°$ to 80° C., preferably from 0° to 40° C. It is however also possible to take a mixture of the starting material III and the acid acceptor in an inert organic solvent and then to run in the aminosulfonyl halide of the formula IV at from $-20°$ to 80° C., preferably from 0° to 40° C. To complete the reaction the mixture is stirred for from 0.5 to 8 hours at from $-20°$ to 80° C., preferably from 0° to 40° C.

The reaction mixture is then concentrated, if necessary, or, in the case of a water-immiscible solvent, is directly extracted with dilute hydrochloric acid and with water to remove the hydrochlorides, giving a sulfonediamide of the formula II.

The compound of the formula II can be cyclized to the desired 1,2,4,6-thiatriazin-5-one-1,1-dioxide salt in an aqueous medium in the presence of an equimolar to 2.5-fold amount of base, or in an organic medium in the presence of an equal to 2.5-fold amount of an alcoholate. To work up the mixture, it is acidified and the precipitate formed is filtered off, if necessary after further concentrating the mixture. The desired end products are thereby obtained in a pure form but can, if necessary, be purified further by recrystallization or chromatography.

Where $R^1$ is hydrogen, the compounds are, according to their spectroscopic data, in the form corresponding to structure I. Depending on the solvent, however, a certain proportion of the tautomeric form Ia may also be present, and since an equilibrium is involved this form is also encompassed by the formula I and claimed together with the compound of the formula I.

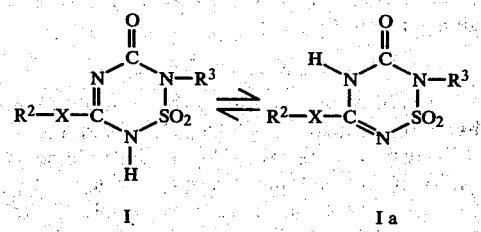

I.    Ia

The substituted isoureas required for the preparation of the starting materials III are known or can be prepared by conventional methods, cf. Beilstein, Edition IV, 3rd supplement, Volume III, pages 146–148. The reaction of these compounds with acyl halides is also known, cf. S. Basterfield and M. S. Whelen, J. Am. chem. Soc. 49 (1927), 3177, and U.S. Pat. No. 4,014,924. By way of example, the following substituted N-carbomethoxy-O-alkyl-isoureas may be prepared by the above methods.

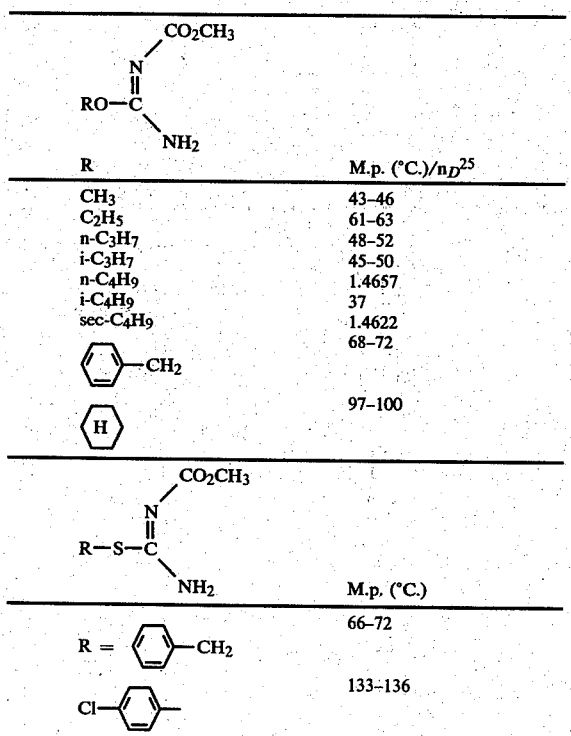

| R | M.p. (°C.)/$n_D^{25}$ |
|---|---|
| $CH_3$ | 43–46 |
| $C_2H_5$ | 61–63 |
| $n-C_3H_7$ | 48–52 |
| $i-C_3H_7$ | 45–50 |
| $n-C_4H_9$ | 1.4657 |
| $i-C_4H_9$ | 37 |
| $sec-C_4H_9$ | 1.4622 |
| phenyl-$CH_2$ | 68–72 |
| H-phenyl | 97–100 |

| R | M.p. (°C.) |
|---|---|
| phenyl-$CH_2$ | 66–72 |
| Cl-phenyl | 133–136 |

The Examples which follow illustrate the preparation of the novel compounds.

EXAMPLE 1

198 parts by weight of methylaminosulfonyl chloride and 162 parts of triethylamine were introduced simultaneously, through 2 feed lines, into a stirred mixture of 202 parts of N-carbomethoxy-O-methylisourea and 1,570 parts of acetonitrile, at 25°–30° C. After stirring the mixture for 3 hours at 25° C., the precipitated hydrochloride was filtered off and the filtrate was concentrated under reduced pressure. The residue was dissolved in 1,500 parts of 1,2-dichloroethane and the solution was extracted once with water and twice with 0.5 N hydrochloric acid. After drying the extract over magnesium sulfate and concentrating it under reduced pressure, 257 parts of N-carbomethoxy-N'-methylsulfamyl-O-methylurea, of $n_D^{25} = 1.4851$, were obtained.

96 parts of this product were dissolved in 235 parts of absolutely dry methanol, 153.5 parts of sodium methylate (30% strength by weight) were added and the mixture was stirred under reflux for 3 hours and then concentrated under reduced pressure. The residue was dissolved in water and the solution was extracted once with ether and then acidified with dilute sulfuric acid. After filtering off the product, washing it with water and drying it, 68 parts (=82.5% of theory) of 6-methyl-3-methoxy-5,6-dihydro-1,2,4,6-thiatriazin-5-one-1,1-dioxide, of melting point 198°–202° C., were obtained. This constitutes active ingredient No. 1.

EXAMPLE 2

37.9 parts of isopropylaminosulfonyl chloride and 26.3 parts of triethylamine were introduced simultaneously, through two feed lines, into a stirred mixture of 54 parts of N-carbomethoxy-S-benzyl-isothiourea and 740 parts of 1,2-dichloroethane, at from 5° to 10° C. After having been stirred for 4 hours at 25° C., the reaction mixture was extracted once with 200 parts of water and twice with 100 parts, each time, of 0.5 N hydrochloric acid. After drying, and concentrating under reduced pressure, 79 parts of N-carbomethoxy-N'-isopropylsulfamyl-S-benzyl-isothiourea of $n_D^{25} = 1.5598$, were obtained. This material crystallized on trituration with hexane, and the crystalline product melted at 76°–78° C. 76 parts of this product were dissolved in a mixture of 44 parts of 50% strength by weight sodium hydroxide solution and 200 parts of water and the reaction mixture was stirred for 5 minutes at 85° C. It was then cooled and acidified with 15% strength hydrochloric acid, and the oil which precipitated was taken up in methylene chloride. This solution was dried over magnesium sulfate, filtered through neutral alumina and concentrated under reduced pressure, giving 59.5 parts of 6-isopropyl-3-benzylmercapto-5,6-dihydro-1,2,4,6-thiatriazin-5-one-1,1-dioxide (86.3% of theory), of melting point 124°–130° C. This constitutes active ingredient No. 2.

EXAMPLE 3

59.6 parts of cyclohexylaminosulfonyl chloride and 26.9 parts of pyridine were introduced through two feed lines, into a stirred solution of 39.6 parts of N-carbomethoxy-O-methylisourea in 300 parts of ethyl acetate, at from 15° to 20° C. After having been stirred for 4 hours at 25° C., the reaction mixture was extracted once with water and once with 0.5 N hydrochloric acid and was then dried and concentrated under reduced pressure. This gave 79 parts of N-carbomethoxy-N'-cyclohexylsulfamyl-O-methylisourea, of $n_D^{25} = 1.4970$. After trituration with a small amount of ether, the compound crystallized, and these crystals melted at 84°–86° C. 15 parts of this product were dissolved in a mixture of 9 parts of 50% strength by weight sodium hydroxide solution and 20 parts of water and the reaction solution was stirred for 4 minutes at from 55° to 60° C. It was then cooled, extracted once with ether, and stirred into a mixture of 9.5 parts of concentrated hydrochloric acid and 10 parts of water. Filtering off the product, washing with water and drying gave 9 parts of 6-cyclohexyl-3-methoxy-5,6-dihydro-1,2,4,6-thiatriazin-5-one-1,1-dioxide, of melting point 173°–177° C. This constitutes active compound No. 3.

EXAMPLE 4

95 parts of isopropylaminosulfonyl chloride were stirred into a mixture of 96 parts of N-carbomethoxy-O-isopropylisourea and 73 parts of triethylamine in 700 parts of tetrahydrofuran in the course of 25 minutes, at 10°–15° C. After having been stirred for one hour at 25° C., the reaction mixture was extracted once with water and once with 0.5 N hydrochloric acid, dried and concentrated under reduced pressure. This gave 130 parts of N-carbomethoxy-N'-isopropylsulfamyl-O-isopropylisourea, of melting point 62°–64° C. 33.7 parts of this product were cyclized by means of 17.6 parts of 50% strength by weight sodium hydroxide solution in 30 parts of water in the course of 5 minutes at from 55° to 60° C. Extraction with ether, acidification, washing with water and drying gave 22 parts of 6-isopropyl-3-isopropoxy-5,6-dihydro-1,2,4,6-thiatriazin-5-one-1,1-dioxide, of melting point 164°–167° C. This constitutes active ingredient No. 4.

EXAMPLE 5

12 parts of 6-isopropyl-3-isopropoxy-5,6-dihydro-1,2,4,6-thiatriazin-5-one-1,1-dioxide were dissolved in a mixture of 10.4 parts of 30% strength by weight sodium methylate and 64 parts of methanol at 25° C. After concentrating this mixture, 13.8 parts of the 2-sodium salt of 6-isopropyl-3-isopropoxy-5,6-dihydro-1,2,4,6-thiatriazin-5-one-1,1-dioxide (melting point 123° C., with decomposition) were obtained. This constitutes active ingredient No. 5.

EXAMPLE 6

140 parts of N-carboxymethyl-N'-methylsulfamyl-O-methylurea, in a mixture of 79.5 parts of sodium carbonate, 450 parts of water and 31 parts by volume of 2 N sodium hydroxide solution, were stirred for 10 minutes at 45° C. The reaction mixture was cooled, extracted with ether and slowly stirred into a mixture of 78 parts of concentrated sulfuric acid in 150 parts of ice water. After filtering off the product, washing it with water and drying it, 81 parts of 6-methyl-3-methoxy-5,6-dihydro-1,2,4,6-thiatriazin-5-one-1,1-dioxide (68% of theory), of melting point 195°–199° C., were obtained. This again constitutes active ingredient No. 1.

The Table which follows gives further examples of the novel compounds.

TABLE

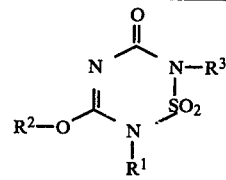

| Active ingredient no. | $R^1$ | $R^2$ | $R^3$ | m.p.(°C.) |
|---|---|---|---|---|
| 6 | H | $CH_3$ | H | |
| 7 | Na | $CH_3$ | $CH_3$ | 246–252 |
| 8 | $NH_4$ | $CH_3$ | $CH_3$ | |
| 9 | H | $CH_3$ | $C_2H_5$ | 167–170 |
| 10 | Na | $CH_3$ | $C_2H_5$ | 143(decomposes) |
| 11 | $NH_2(CH_2CH_2OH)_2$ | $CH_3$ | $C_2H_5$ | |
| 12 | H | $CH_3$ | n-$C_3H_7$ | 137–140 |
| 13 | Na | $CH_3$ | n-$C_3H_7$ | 214(decomposes) |
| 14 | H | $CH_3$ | i-$C_3H_7$ | 146–150 |
| 15 | Na | $CH_3$ | i-$C_3H_7$ | 265(decomposes) |
| 16 | H | $CH_3$ | ▷ | |
| 17 | H | $CH_3$ | n-$C_4H_9$ | 128–132 |
| 18 | Na | $CH_3$ | n-$C_4H_9$ | 219(decomposes) |
| 19 | H | $CH_3$ | i-$C_4H_9$ | |
| 20 | Na | $CH_3$ | i-$C_4H_9$ | |
| 21 | H | $CH_3$ | sec-$C_4H_9$ | |
| 22 | Na | $CH_3$ | sec-$C_4H_9$ | |
| 23 | H | $CH_3$ | tert-$C_4H_9$ | |
| 24 | Na | $CH_3$ | tert-$C_4H_9$ | |
| 25 | Na | $CH_3$ | ⟨H⟩ | 216–220 |
| 26 | H | $CH_3$ | $CH_2-CH_2Cl$ | |
| 27 | H | $CH_3$ | $-CH-CH-Cl$ <br> $\quad\;\, CH_3\; CH_3$ | |
| 28 | H | $CH_3$ | $-CH-CH_3$ <br> $\quad\;\, CH_2F$ | |
| 29 | H | $CH_3$ | $CH_2-CH_2-O-CH_3$ | 180–182 |
| 30 | Na | $CH_3$ | $-CH_2-CH_2-O-CH_3$ | 111–115 |
| 31 | H | $C_2H_5$ | H | |

TABLE-continued

| | | | | |
|---|---|---|---|---|
| 32 | H | C₂H₅ | CH₃ | 168–171 |
| 33 | Na | C₂H₅ | CH₃ | |
| 34 | NH₂(C₂H₅)₂ | C₂H₅ | CH₃ | |
| 35 | H | C₂H₅ | C₂H₅ | |
| 36 | Na | C₂H₅ | C₂H₅ | |
| 37 | H | C₂H₅ | n-C₃H₇ | 122–125 |
| 38 | Na | C₂H₅ | n-C₃H₇ | |
| 39 | H | C₂H₅ | i-C₃H₇ | 154–158 |
| 40 | Na | C₂H₅ | i-C₃H₇ | 116(decomposes) |
| 41 | H | C₂H₅ | ▷ | |
| 42 | H | C₂H₅ | n-C₄H₉ | |
| 43 | H | C₂H₅ | i-C₄H₉ | |
| 44 | NH₄ | C₂H₅ | i-C₄H₉ | |
| 45 | H | C₂H₅ | sec-C₄H₉ | |
| 46 | H | C₂H₅ | tert-C₄H₉ | |
| 47 | H | n-C₃H₇ | H | |
| 48 | H | n-C₃H₇ | CH₃ | |
| 49 | Na | n-C₃H₇ | CH₃ | 155–160 |
| 50 | H | n-C₃H₇ | C₂H₅ | 117–123 |
| 51 | H | n-C₃H₇ | i-C₃H₇ | 162–166 |
| 52 | Na | n-C₃H₇ | i-C₃H₇ | 152 |
| 53 | H | n-C₃H₇ | n-C₃H₇ | |
| 54 | K | n-C₃H₇ | n-C₃H₇ | |
| 55 | H | n-C₃H₇ | n-C₄H₉ | |
| 56 | NH₄ | n-C₃H₇ | i-C₄H₉ | |
| 57 | H | n-C₃H₇ | sec-C₄H₉ | |
| 58 | H | n-C₃H₇ | tert-C₄H₉ | |
| 59 | H | n-C₃H₇ | CH₂CH₂OCH₃ | |
| 60 | H | i-C₃H₇ | H | |
| 61 | H | i-C₃H₇ | CH₃ | 174–176 |
| 62 | Na | i-C₃H₇ | CH₃ | 305(decomposes) |
| 63 | H | i-C₃H₇ | C₂H₅ | |
| 64 | H | i-C₃H₇ | n-C₃H₇ | 107–111 |
| 65 | H | i-C₃H₇ | sec-C₄H₉ | |
| 66 | H | i-C₃H₇ | tert-C₄H₉ | |
| 67 | H | n-C₄H₉ | H | |
| 68 | H | n-C₄H₉ | CH₃ | 112–116 |
| 69 | Na | n-C₄H₉ | CH₃ | 156–160 |
| 70 | H | n-C₄H₉ | C₂H₅ | 117–123 |
| 71 | H | n-C₄H₉ | n-C₃H₇ | |
| 72 | H | n-C₄H₉ | n-C₃H₇ | |
| 73 | H | i-C₄H₉ | H | |
| 74 | H | i-C₄H₉ | CH₃ | 138(decomposes) |
| 75 | NH₄ | i-C₄H₉ | CH₃ | |
| 76 | H | i-C₄H₉ | C₂H₅ | |
| 77 | Na | i-C₄H₉ | C₂H₅ | |
| 78 | H | i-C₄H₉ | n-C₃H₇ | |
| 79 | H | i-C₄H₉ | i-C₃H₇ | 131–135 |
| 80 | Na | i-C₄H₉ | i-C₃H₇ | 163(decomposes) |
| 81 | H | i-C₄H₉ | sec-C₄H₉ | |
| 82 | H | i-C₄H₉ | —CH(CH₃)CH₂F | |
| 83 | H | i-C₄H₉ | CH₂—CH₂—Cl | |
| 84 | H | i-C₄H₉ | CH₂—CH₂—O—CH₃ | |
| 85 | H | sec-C₄H₉ | H | |
| 86 | H | sec-C₄H₉ | CH₃ | 114–118 |
| 87 | Na | sec-C₄H₉ | CH₃ | 172(decomposes) |
| 88 | H | sec-C₄H₉ | C₂H₅ | |
| 89 | H | sec-C₄H₉ | n-C₃H₇ | |
| 90 | H | sec-C₄H₉ | i-C₃H₇ | 132–135 |
| 91 | Na | sec-C₄H₉ | i-C₃H₇ | 178(decomposes) |
| 92 | H | sec-C₄H₉ | n-C₄H₉ | |
| 93 | H | sec-C₄H₉ | CH₂—CH₂Cl | |
| 94 | H | sec-C₄H₉ | —CH(CH₃)CH₂F | |
| 95 | H | sec-C₄H₉ | CH₂—CH₂—O—CH₃ | |
| 96 | H | C₆H₅—CH₂ | H | |
| 97 | Na | C₆H₅—CH₂ | CH₃ | |
| 98 | H | C₆H₅—CH₂ | C₂H₅ | |
| 99 | H | C₆H₅—CH₂ | i-C₃H₇ | |

TABLE-continued

| No. | R¹ | R² | R³ | m.p.(°C.) |
|---|---|---|---|---|
| 100 | H | (2-Cl,6-F-C₆H₃)—CH₂— | $CH_3$ | |
| 101 | H | (2,6-F₂-C₆H₃)—CH₂— | $CH_3$ | |
| 102 | H | $C_6H_5$—$CH_2$ | $CH_3$ | |
| 103 | H | $CH_2$=CH—$CH_2$ | H | |
| 104 | Na | $CH_2$=CH—$CH_2$ | $CH_3$ | |
| 105 | H | $CH_2$=CH—$CH_2$ | $CH_3$ | |
| 106 | H | $CH_2$=CH—$CH_2$ | $C_2H_5$ | |
| 107 | H | $CH_2$=CH—$CH_2$ | $i$-$C_3H_7$ | |
| 108 | H | $CH_3$—CH=CH—$CH_2$ | H | |
| 109 | H | $CH_3$—CH=CH—$CH_2$ | $CH_3$ | |
| 110 | H | $CH_3$—CH=CH—$CH_2$ | $i$-$C_3H_7$ | |
| 111 | H | $CH_2$=C($CH_3$)—$CH_2$ | H | |
| 112 | H | $CH_2$=C($CH_3$)—$CH_2$ | $CH_3$ | |
| 113 | H | $CH_2$=C($CH_3$)—$CH_2$ | $C_2H_5$ | |
| 114 | H | $CH_2$=C($CH_3$)—$CH_2$ | $i$-$C_3H_7$ | |
| 115 | H | H—C≡C—$CH_2$ | H | |
| 116 | H | H—C≡C—$CH_2$ | $CH_3$ | |
| 117 | Na | H—C≡C—$CH_2$ | $C_2H_5$ | |
| 118 | H | H—C≡C—$CH_2$ | $i$-$C_3H_7$ | |
| 119 | H | HC≡C—CH($CH_3$)— | H | |
| 120 | H | HC≡C—CH($CH_3$)— | $CH_3$ | |
| 121 | H | $H_2C$=CH—CH($CH_3$)— | $CH_3$ | |
| 122 | H | $H_2C$=CH—CH($CH_3$)— | $C_2H_5$ | |
| 123 | H | cyclohexyl— | $i$-$C_3H_7$ | 159–163 |
| 124 | H | cyclohexyl— | $CH_3$ | 172–174 |
| 125 | H | (tetrahydrofuran-2-yl)—$CH_2$— | $i$-$C_3H_7$ | 140–143 |

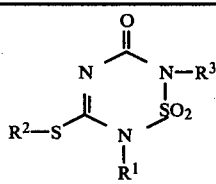

| Active ingredient no. | R¹ | R² | R³ | m.p.(°C.) |
|---|---|---|---|---|
| 126 | Na | $C_6H_5CH_2$ | $CH_3$ | 236(decomposes) |
| 127 | H | $C_6H_5CH_2$ | $CH_3$ | 202–206 |
| 128 | H | $C_6H_5CH_2$ | $C_2H_5$ | |

TABLE-continued

| # | | | | |
|---|---|---|---|---|
| 129 | Na | $C_6H_5CH_2$ | i-$C_3H_7$ | 127(decomposes) |
| 130 | H | 2-Cl, 6-F-$C_6H_3$-$CH_2$ | $CH_3$ | |
| 131 | H | 2,6-di-F-$C_6H_3$-$CH_2$ | $CH_3$ | |
| 132 | H | $C_6H_5$ | i-$C_3H_7$ | 186–188 |
| 133 | Na | 4-(CH$_3$)$_3$C-$C_6H_4$- | i-$C_3H_7$ | 125–130 |
| 134 | Na | 4-Cl-$C_6H_4$- | $CH_3$ | 250(decomposes) |

The novel active ingredients can be converted into the conventional formulations, e.g. solutions, emulsions, suspensions, dusts, powders, pastes and granules. The form of application depends entirely on the purpose for which the agents are being used; it should, however, ensure a fine and uniform distribution of the active ingredient. The formulations are prepared in the conventional manner, for example by diluting the active ingredient with solvent and/or carriers, with or without the addition of emulsifiers and dispersants and, where water is used as the diluent, with or without organic auxiliary solvents. Suitable auxiliaries are, essentially, solvents, for example aromatics, e.g., xylene and benzene, chloroaromatics, e.g. chlorobenzene, paraffins, e.g. petroleum fractions, alcohols, e.g. methanol and butanol, amines e.g., ethanolamine, dimethylformamide, and water; solid carriers, for example natural rock powders, e.g., kaolin, alumina, talc and chalk, and synthetic rock powders, e.g. highly disperse silica and silicates; emulsifiers, for example non-ionic and anionic emulsifiers, e.g. polyoxyethylene fatty alcohol ethers, alkylsulfonates and arylsulfonates, and dispersants, for example lignin, sulfite waste liquors and methylcellulose.

The agents in general contain from 0.1 to 95% by weight of active ingredient, preferably from 0.5 to 90%.

Application rates depend on the composition and growth stages of the weed flora, and vary from 0.1 to 15, preferably 0.2 to 5, kg of active ingredient per hectare; for total plant destruction, the higher rates should be used.

The agents, and the ready-to-use preparations obtained therefrom, e.g., solutions, emulsions, suspensions, powders, dusts, pastes or granules, are applied in conventional manner, e.g. by spraying, atomizing, dusting, broadcasting or watering.

Examples of such formulations are given below.

I. 90 parts by weight of the compound of Example 1 is mixed with 10 parts by weight of N-methyl-α-pyrrolidone. A mixture is obtained which is suitable for application in the form of very fine drops.

II. 20 parts by weight of the compound of Example 2 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

III. 20 parts by weight of the compound of Example 3 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

IV. 20 parts by weight of the compound of Example 4 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

V. 20 parts by weight of the compound of Example 1 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of the compound of Example 2 is intimately mixed with 97 parts by weight of particulate kaolin. A dust is obtained containing 3% by weight of the active ingredient.

VII. 30 parts by weight of the compound of Example 3 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of the compound of Example 4 is intimately mixed with 10 parts of the sodium salt of a phenolsulfonic acid-urea-formaldehyde condensate, 2 parts of silica gel and 48 parts of water. Dilution in 100,000 parts by weight of water gives an aqueous dispersion containing 0.04 wt% of active ingredient.

IX. 20 parts of the compound of Example 1 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The new 5,6-dihydro-1,2,4,6-thiatriazin-5-one-1,1-dioxides may be mixed and applied together with numerous representatives of other herbicidal or growth-regulating active ingredient groups. Examples of suitable mixture components are diazines, benzothiadiazinones, 2,6-dinitroanilines, N-phenylcarbamates, biscarbamates, thiolcarbamates, halocarboxylic acids, triazines, amides, ureas, diphenyl ethers, triazinones, uracils, benzofuran derivatives, etc. Such combinations broaden the spectrum of action and synergistic effects are sometimes achieved. Mixtures may be prepared with, for example, the following compounds:

5-amino-4-chloro-2-phenyl-3(2H)-pyridazinone
5-amino-4-bromo-2-phenyl-3(2H)-pyridazinone
5-amino-4-chloro-2-cyclohexyl-3(2H)-pyridazinone
5-amino-4-bromo-2-cyclohexyl-3(2H)-pyridazinone
5-methylamino-4-chloro-2-(3-trifluoromethylphenyl)-3(2H)-pyridazinone
5-methylamino-4-chloro-2-(3-α,α,β,β-tetrafluoroethoxyphenyl)-3(2H)-pyridazinone
5-dimethylamino-4-chloro-2-phenyl-3(2H)-pyridazinone
4,5-dimethoxy-2-phenyl-3(2H)-pyridazinone
4,5-dimethoxy-2-cyclohexyl-3(2H)-pyridazinone
4,5-dimethoxy-2-(3-trifluoromethylphenyl)-3(2H)-pyridazinone
5-methoxy-4-chloro-2-(3-trifluoromethylphenyl)-3(2H)-pyridazinone
5-amino-4-bromo-2(3-methylphenyl)-3(2H)-pyridazinone
3-(1-methylethyl)-1H-2,1,3-benzothiadiazin-4(3H)-one-2,2-dioxide and salts
3-(1-methylethyl)-8-chloro-1H-2,1,3-benzothiadiazin-4(3H)-one-2,2-dioxide and salts
3-(1-methylethyl)-8-fluoro-1H-2,1,3-benzothiadiazin-4(3H)-one-2,2-dioxide and salts
3-(1-methylethyl)-8-methyl-1H-2,1,3-benzothiadiazin-4(3H)-one-2,2-dioxide and salts
1-methoxymethyl-3-(1-methylethyl)-2,1,3-benzothiadiazin-4(3H)-one-2,2-dioxide
1-methoxymethyl-8-chloro-3-(1-methylethyl)-2,1,3-benzothiadiazin-4(3H)-one-2,2-dioxide
1-methoxymethyl-8-fluoro-3-(1-methylethyl)-2,1,3-benzothiadiazin-4(3H)-one-2,2-dioxide
1-cyano-8-chloro-3-(1-methylethyl)-2,1,3-benzothiadiazin-4(3H)-one-2,2-dioxide
1-cyano-8-fluoro-3-(1-methylethyl)-2,1,3-benzothiadiazin-4(3H)-one-2,2-dioxide
1-cyano-8-methyl-3-(1-methylethyl)-2,1,3-benzothiadiazin-4(3H)-one-2,2-dioxide
1-cyano-3-(1-methylethyl)-2,1,3-benzothiadiazin-4(3H)-one-2,2-dioxide
1-azidomethyl-3-(1-methylethyl)-2,1,3-benzothiadiazin-4(3H)-one-2,2-dioxide
3-(1-methylethyl)-1H-pyridino-[3,2-e]-2,1,3-thiadiazin-(4)-one-2,2-dioxide
N-(1-ethylpropyl)-2,6-dinitro-3,4-dimethylaniline
N-(1-methylethyl)-N-ethyl-2,6-dinitro-4-trifluoromethylaniline
N-n-propyl-N-β-chloroethyl-2,6-dinitro-4-trifluoromethylaniline
N-n-propyl-N-cyclopropylmethyl-2,6-dinitro-4-trifluoromethylaniline
N-bis-(n-propyl)-2,6-dinitro-3-amino-4-trifluoromethylaniline
N-bis-(n-propyl)-2,6-dinitro-4-methylaniline
N-bis-(n-propyl)-2,6-dinitro-4-methylsulfonylaniline
N-bis-(n-propyl)-2,6-dinitro-4-aminosulfonylaniline
bis-(β-chloroethyl)-2,6-dinitro-4-methylaniline
N-ethyl-N-(2-methylallyl)-2,6-dinitro-4-trifluoromethylaniline
3,4-dichlorobenzyl N-methylcarbamate
2,6-di-tert.butyl-4-methylphenyl N-methylcarbamate
isopropyl N-phenylcarbamate
3-methoxyprop-2-yl N-3-fluorophenylcarbamate
isopropyl N-3-chlorophenylcarbamate
but-1-yn-3-yl N-3-chlorophenylcarbamate
4-chlorobut-2-yn-1-yl N-3-chlorophenylcarbamate
methyl N-3,4-dichlorophenylcarbamate
methyl N-(4-aminobenzenesulfonyl)-carbamate
O-(N-phenylcarbamoyl)-propanone oxime
N-ethyl-2-(phenylcarbamoyl)-oxypropionic acid amide
3'-N-isopropylcarbamoyloxypropionanilide
ethyl-N-(3-(N'-phenylcarbamoyloxy)-phenyl)-carbamate
methyl-N-(3-(N'-methyl-N-phenylcarbamoyloxy)-phenyl)-carbamate
isopropyl-N-(3-(N'-ethyl-N'-phenylcarbamoyloxy)-phenyl)-carbamate
methyl-N-(3-(N'-3-methylphenylcarbamoyloxy)-phenyl)-carbamate
methyl-N-(3-(N'-4-fluorophenylcarbamoyloxy)-phenyl)-carbamate
methyl-N-(3-(N'-3-chloro-4-fluorophenylcarbamoyloxy)-phenyl)-carbamate
ethyl-N-[3-N'-(3-chloro-4-fluorophenylcarbamoyloxy)-phenyl]-carbamate
ethyl-N-[3-N'-(3,4-difluorophenylcarbamoyloxy)-phenyl]-carbamate
methyl-N-[3-(N'-3,4-difluorophenylcarbamoyloxy)-phenyl]-carbamate
methyl N-3-(4'-fluorophenoxycarbonylamino)-phenylcarbamate
ethyl N-3-(2'-methylphenoxycarbonylamino)-phenylcarbamate
methyl N-3-(4'-fluorophenoxycarbonylamino)-phenylthiolcarbamate
methyl N-3-(2',4',5'-trimethylphenoxycarbonylamino)-phenylthiolcarbamate
methyl N-3-(phenoxycarbonylamino)-phenylthiolcarbamate
p-chlorobenzyl N,N-diethylthiolcarbamate
ethyl N,N-di-n-propylthiolcarbamate
n-propyl N,N-di-n-propylthiolcarbamate
2,3-dichloroallyl N,N-diisopropylthiolcarbamate
2,3,3-trichloroallyl N,N-diisopropylthiolcarbamate
3-methyl-5-isoxazolylmethyl N,N-diisopropylthiolcarbamate
3-ethyl-5-isoxazolylmethyl N,N-diisopropylthiolcarbamate
ethyl N,N-di-sec.-butylthiolcarbamate
benzyl N,N-di-sec.-butylthiolcarbamate
ethyl N-ethyl-N-cyclohexylthiolcarbamate
ethyl N-ethyl-N-bicyclo-[2.1.1]-heptylthiolcarbamate S-(2,3,3-trichloroallyl)-(2,2,4-trimethylazetidine)-1-carbothiolate
S-ethylhexahydro-1-H-azepine-1-carbothiolate
S-benzyl-(3-methylhexahydro-1-H-azepine-1)-carbothiolate
S-benzyl-(2,3-dimethylhexahydro-1-H-azepine-1)-carbothiolate
S-ethyl-(3-methylhexahydro-1-H-azepine-1)-carbothiolate
n-propyl N-ethyl-N-n-butylthiolcarbamate
2-chloroallyl N,N-dimethyldithiocarbamate
N-methyldithiocarbamic acid, sodium salt
trichloroacetic acid, sodium salt
α,α-dichloropropionic acid, sodium salt
α,α-dichlorobutyric acid, sodium salt
α,α-β,β-tetrafluoropropionic acid, sodium salt
α-methyl-α,β-dichloropropionic acid, sodium salt
methyl-α-chloro-β-(4-chlorophenyl)-propionate
methyl α,β-dichloro-β-phenylpropionate
benzamido oxyacetic acid
2,3,5-triiodobenzoic acid (salts, esters, amides)
2,3,6-trichlorobenzoic acid (salts, esters, amides)
2,3,5,6-tetrachlorobenzoic acid (salts, esters, amides)
2-methoxy-3,6-dichlorobenzoic acid (salts, esters, amides)
2-methoxy-3,5,6-trichlorobenzoic acid (salts, esters, amides)
3-amino-2,5,6-trichlorobenzoic acid (salts, esters, amides)
O,S-dimethyltetrachlorothioterephthalate
dimethyl-2,3,5,6-tetrachloroterephthalate
disodium 3,6-endoxohexahydrophthalate
4-amino-3,5,6-trichloropicolinic acid (salts)
ethyl 2-cyano-3-(N-methyl-N-phenyl)-aminoacrylate
isobutyl 2-[4-(4'-chlorophenoxy)-phenoxy]-propionate
methyl 2-[4-(2',4'-dichlorophenoxy)-phenoxy]-propionate
methyl 2-[4-(4'-trifluoromethylphenoxy)-phenoxy]-propionate
2-[4-(2'-chloro-4'-trifluorophenoxy)-phenoxy]-propionic acid, sodium salt
2-[4-(3',5'-dichloropyridyl-2-oxy)-phenoxy]-propionic acid, sodium salt
ethyl 2-(N-benzoyl-3,4-dichlorophenylamino)-propionate
methyl-2-(N-benzoyl-3-chloro-4-fluorophenylamino)-propionate
isopropyl 2-(N-benzoyl-3-chloro-4-fluorophenylamino)-propionate
2-chloro-4-ethylamino-6-isopropylamino-1,3,5-triazine
2-chloro-4-ethylamino-6-(amino-2'-propionitrile)-1,3,5-triazine
2-chloro-4-ethylamino-6-(2-methoxypropyl)-2-amino-1,3,5-triazine
2-chloro-4-ethylamino-6-butyn-1-yl-2-amino-1,3,5-triazine
2-chloro-4,6-bisethylamino-1,3,5-triazine
2-chloro-4,6-bisisopropylamino-1,3,5-triazine
2-chloro-4-isopropylamino-6-cyclopropylamino-1,3,5-triazine
2-azido-4-methylamino-6-isopropylamino-1,3,5-triazine
2-methylthio-4-ethylamino-6-isopropylamino-1,3,5-triazine
2-methylthio-4-ethylamino-6-tert.butylamino-1,3,5-triazine
2-methylthio-4,6-bisethylamino-1,3,5-triazine
2-methylthio-4,6-bisisopropylamino-1,3,5-triazine
2-methoxy-4-ethylamino-6-isopropylamino-1,3,5-triazine
2-methoxy-4,6-bisethylamino-1,3,5-triazine
2-methoxy-4,6-bisisopropylamino-1,3,5-triazine
4-amino-6-tert.butyl-3-methylthio-4,5-dihydro-1,2,4-triazin-5-one
4-amino-6-phenyl-3-methyl-4,5-dihydro-1,2,4-triazin-5-one
4-isobutylidenamino-6-tert.butyl-3-methylthio-4,5-dihydro-1,2,4-triazin-5-one
1-methyl-3-cyclohexyl-6-dimethylamino-1,3,5-triazin-2,4-dione
3-tert.butyl-5-chloro-6-methyluracil
3-tert.butyl-5-bromo-6-methyluracil
3-isopropyl-5-bromo-6-methyluracil
3-sec.butyl-5-bromo-6-methyluracil
3-(2-tetrahydropyranyl)-5-chloro-6-methyluracil
3-(2-tetrahydropyranyl)-5,6-trimethyleneuracil
3-cyclohexyl-5,6-trimethyleneuracil
2-methyl-4-(3'-trifluoromethylphenyl)-tetrahydro-1,2,4-oxadiazine-3,5-dione
2-methyl-4-(4'-fluorophenyl)-tetrahydro-1,2,4-oxadiazine-3,5-dione
3-amino-1,2,4-triazole
1-allyloxy-1-(4-bromophenyl)-2-[1', 2', 4'-triazolyl-(1')]-ethane (salts)
1-(4-chlorophenoxy)-3,3-dimethyl-1-(1H-1,2,3-triazol-1-yl)-butan-2-one
N,N-diallylchloroacetamide
N-isopropyl-2-chloroacetanilide
N-(but-1-yn-3-yl)-2-chloroacetanilide
2-methyl-6-ethyl-N-propargyl-2-chloroacetanilide
2-methyl-6-ethyl-N-ethoxymethyl-2-chloroacetanilide
2-methyl-6-ethyl-N-(2-methoxy-1-methylethyl)-2-chloroacetanilide
2-methyl-6-ethyl-N-(isopropoxycarbonylethyl)-2-chloroacetanilide
2-methyl-6-ethyl-N-(4-methoxypyrazol-1-yl-methyl)-2-chloroacetanilide
2-methyl-6-ethyl-N-(pyrazol-1-yl-methyl)-2-chloroacetanilide
2,6-dimethyl-N-(pyrazon-1-yl-methyl)-2-chloroacetanilide
2,6-dimethyl-N-(4-methylpyrazol-1-yl-methyl)-2-chloro-acetanilide
2,6-dimethyl-N-(1,2,4-triazol-1-yl-methyl)-2-chloroacetanilide
2,6-dimethyl-N-(3,5-dimethylpyrazol-1-yl-methyl)-2-chloroacetanilide
2,6-dimethyl-N-(1,3-dioxolan-2-yl-methyl)-2-chloroacetanilide
2,6-dimethyl-N-(2-methoxyethyl)-2-chloroacetanilide
2,6-dimethyl-N-isobutoxymethyl-2-chloroacetanilide
2,6-diethyl-N-methoxymethyl-2-chloroacetanilide
2,6-diethyl-N-n-butoxymethyl-2-chloroacetanilide
2,6-diethyl-N-ethoxycarbonylmethyl-2-chloroacetanilide
2,3,6-trimethyl-N-(pyrazol-1-yl-methyl)-2-chloroacetanilide
2,3-dimethyl-N-isopropyl-2-chloroacetanilide
2,6-diethyl-N-(propoxyethyl)-2-chloroacetanilide
2-(2-methyl-4-chlorophenoxy-N-methoxyacetamide
2-(α-naphthoxy)-N,N-diethylpropionamide
2,2-diphenyl-N,N-dimethylacetamide
α-(3,4,5-tribromopyrazol-1-yl)-N,N-dimethylpropionamide
N-(1,1-dimethylpropynyl)-3,5-dichlorobenzamide
N-1-naphthylphthalamic acid propionic acid 3,4-dichloroanilide
cyclopropanecarboxylic acid 3,4-dichloroanilide
methacrylic acid 3,4-dichloroanilide
2-methylpentanecarboxylic acid 3,4-dichloroanilide
N-2,4-dimethyl-5-(trifluoromethyl)-sulfonylamino-phenylacetamide
N-4-methyl-5-(trifluoromethyl)-sulfonylamino-phenylacetamide
2-propionylamino-4-methyl-5-chlorothiazole
O-(methylsulfonyl)-glycolic acid N-ethoxymethyl-2,6-dimethylanilide
O-(methylaminosulfonyl)-glycolic acid N-isopropylanilide
O-(isopropylaminosulfonyl)-glycolic acid N-but-1-yn-3-yl-anilide
O-(methylaminosulfonyl)-glycolic acid hexamethyleneamide
2,6-dichlorothiobenzamide
2,6-dichlorobenzonitrile
3,5-dibromo-4-hydroxybenzonitrile (salts)
3,5-diiodo-4-hydroxybenzonitrile (salts)
3,5-dibromo-4-hydroxy-O-2,4-dinitrophenylbenzaldoxime (salts)
3,5-dibromo-4-hydroxy-O-2-cyano-4-nitrophenylbenzaldoxime (salts)
pentachlorophenol, sodium salt
2,4-dichlorophenyl-4'-nitrophenyl ether
2,4,6-trichlorophenyl-4'-nitrophenyl ether
2-fluoro-4,6-dichlorophenyl-4'-nitrophenyl ether
2-chloro-4-trifluoromethylphenyl-4'-nitrophenyl ether
2,4'-dinitro-4-trifluoromethyl-diphenyl ether
2,4-dichlorophenyl-3'-methoxy-4'-nitro-phenyl ether
2-chloro-4-trifluoromethylphenyl-3'-ethoxy-4'-nitrophenyl ether
2-chloro-4-trifluoromethylphenyl-3'-carboxy-4'-nitrophenyl ether (salts)
2,4-dichlorophenyl-3'-methoxycarbonyl-4'-nitro-phenyl ether
2-(3,4-dichlorophenyl)-4-methyl-1,2,4-oxadiazolidine-3,5-dione
2-(3-tert.butylcarbamoyloxyphenyl)-4-methyl-1,2,4-oxadiazolidine-3,5-dione
2-(3-isopropylcarbamoyloxyphenyl)-4-methyl-1,2,4-oxadiazolidine-3,5-dione
2-phenyl-3,1-benzoxazinone-(4)
(4-bromophenyl)-3,4,5,9,10-pentaazatetracyclo-[5,4,1,O$^{2,6}$,O$^{8,11}$]-dodeca-3,9-diene
2-ethoxy-2,3-dihydro-3,3-dimethyl-5-benzofuranylmethane sulfonate
2-ethoxy-2,3-dihydro-3,3-dimethyl-5-benzofuranyl-dimethylaminosulfate
2-ethoxy-2,3-dihydro-3,3-dimethyl-5-benzofuranyl-(N-methyl-N-acetyl)-aminosulfonate
3,4-dichloro-1,2-benzisothiazole
N-4-chlorophenyl-allylsuccinimide
2-methyl-4,6-dinitrophenol (salts, esters)
2-sec.butyl-4,6-dinitrophenol (salts, esters)
2-sec.butyl-4,6-dinitrophenol acetate
2-tert.butyl-4,6-dinitrophenol acetate
2-tert.butyl-4,6-dinitrophenol (salts)
2-tert.butyl-5-methyl-4,6-dinitrophenol (salts)
2-tert.butyl-5-methyl-4,6-dinitrophenol acetate
2-sec.amyl-4,6-dinitrophenol (salts, esters)
1-(α,α-dimethylbenzyl)-3-(4-methylphenyl)-urea
1-3-(2-methylcyclohexyl)-urea
1-phenyl-1-benzoyl-3,3-dimethylurea
1-(4-chlorophenyl)-1-benzoyl-3,3-dimethylurea
1-(4-chlorophenyl)-3,3-dimethylurea
1-(4-chlorophenyl)-3-methyl-3-but-1-yn-3-yl-urea
1-(3,4-dichlorophenyl)-3,3-dimethylurea
1-(3,4-dichlorophenyl)-1-benzoyl-3,3-dimethylurea
1-(3,4-dichlorophenyl)-3-methyl-3-n.butylurea
1-(4-isopropylphenyl)-3,3-dimethylurea
1-(3-trifluoromethylphenyl)-3,3-dimethylurea
1-(α,α,β,β-tetrafluoroethoxyphenyl)-3,3-dimethylurea
1-(3-tert.butylcarbamoyloxyphenyl)-3,3-dimethylurea
1-(3-chloro-4-methylphenyl)-3,3-dimethylurea
1-(3-chloro-4-methoxyphenyl)-3,3-dimethylurea
1-(3,5-dichloro-4-methoxyphenyl)-3,3-dimethylurea
1-[4-(4'-chlorophenoxy)-phenyl]-3,3-dimethylurea
1-[4-(4'-methoxyphenoxy)-phenyl]-3,3-dimethylurea
1-cyclooctyl-3,3-dimethylurea
1-(hexahydro-4,7-methanoindan-5-yl)-3,3-dimethylurea
1-[1- or 2-(3a,4,5,7,7a-hexahydro)-4,7-methanoindanyl]-3,3-dimethylurea
1-(4-fluorophenyl)-3-carboxymethoxy-3-methylurea
1-phenyl-3-methyl-3-methoxyurea
1-(4-chlorophenyl)-3-methyl-3-methoxyurea
1-(4-bromophenyl)-3-methyl-3-methoxyurea
1-(3,4-dichlorophenyl)-3-methyl-3-methoxyurea
1-(3-chloro-4-bromophenyl)-3-methyl-3-methoxyurea
1-(3-chloro-4-isopropylphenyl)-3-methyl-3-methoxyurea
1-(3-chloro-4-methoxyphenyl)-3-methyl-3-methoxyurea
1-(3-tert.butylphenyl)-3-methyl-3-methoxyurea
1-(2-benzthiazolyl)-1,3-dimethylurea
1-(2-benzthiazolyl)-3-methylurea
1-(5-trifluoromethyl-1,3,4-thiadiazolyl)-1,3-dimethylurea
imidazolidin-2-one-1-carboxylic acid isobutylamide
1,2-dimethyl-3,5-diphenylpyrazolium-methylsulfate
1,2,4-trimethyl-3,5-diphenylpyrazolium-methylsulfate
1,2-dimethyl-4-bromo-3,5-diphenylpyrazolium-methylsulfate
1,3-dimethyl-4-(3,4-dichlorobenzoyl)-5-(4-methylphenylsulfonyloxy)-pyrazole
2,3,5-trichloropyridinol-(4)
1-methyl-3-phenyl-5-(3'-trifluoromethylphenyl)-pyridone-(4)
1-methyl-4-phenylpyridinium chloride
1,1-dimethylpyridinium chloride
3-phenyl-4-hydroxy-6-chloropyridazine
1,1'-dimethyl-4,4'-dipyridylium-di(methylsulfate)
1,1'-di-(3,5-dimethylmorpholine-carbonylmethyl)-4,4'-dipyridylium dichloride
1,1'-ethylene-2,2'-dipyridylium dibromide
3-[1-(N-ethoxyamino)-propylidene]-6-ethyl-3,4-dihydro-2H-pyran-2,4-dione
3-[1-(N-allyloxyamino)-propylidene]-6-ethyl-3,4-dihydro-2H-pyran-2,4-dione
2-[1-(N-allyloxyamino)-propylidene]-5,5-dimethylcyclohexane-1,3-dione (salts)
2-[1-(N-allyloxyamino-butylidene]-5,5-dimethylcyclohexane-1,3-dione (salts)
2-[1-(N-allyloxyamino-butylidene]-5,5-dimethyl-4-methoxycarbonyl-cyclohexane-1,3-dione (salts)
2-chlorophenoxyacetic acid (salts, esters, amides)
4-chlorophenoxyacetic acid (salts, esters, amides)
2,4-dichlorophenoxyacetic acid (salts, esters, amides)
2,4,5-trichlorophenoxyacetic acid (salts, esters, amides)
2-methyl-4-chlorophenoxyacetic acid (salts, esters, amides)
3,5,6-trichloro-2-pyridinyl-oxyacetic acid (salts, esters, amides)
methyl α-naphthoxyacetate 2-(2-methylphenoxy)-propionic acid (salts, esters, amides)
2-(4-chlorophenoxy)-propionic acid (salts, esters, amides)
2-(2,4-dichlorophenoxy)-propionic acid (salts, esters, amides)
2-(2,4,5-trichlorophenoxy)-propionic acid (salts, esters, amides)
2-(2-methyl-4-chlorophenoxy)-propionic acid (salts, esters, amides)
4-(2,4-dichlorophenoxy)-butyric acid (salts, esters, amides)
4-(2-methyl-4-chlorophenoxy)-butyric acid (salts, esters, amides)
cyclohexyl-3-(2,4-dichlorophenoxy)-acrylate
9-hydroxyfluorenecarboxylic acid-(9) (salts, esters)
2,3,6-trichlorophenylacetic acid (salts, esters)
4-chloro-2-oxobenzothiazolin-3-yl-acetic acid (salts, esters)
gibelleric acid (salts)
disodium methylarsonate
monosodium salt of methylarsonic acid
N-phosphonomethyl-glycine (salts)
N,N-bis-(phosphonomethyl)-glycine (salts)
2-chloroethyl 2-chloroethanephosphonate
ammonium-ethyl-carbamoyl-phosphonate
di-n-butyl-1-n-butylamino-cyclohexyl-phosphonate
trithiobutylphosphite
O,O-diisopropyl-5-(2-benzosulfonylaminoethyl)-phosphorodithionate
2,3-dihydro-5,6-dimethyl-1,4-dithiin-1,1,4,4-tetraoxide
5-tert.butyl-3-(2,4-dichloro-5-isopropoxyphenyl)-1,3,4-oxadiazolone-(2)
4,5-dichloro-2-trifluoromethylbenzimidazole (salts)
1,2,3,6-tetrahydropyridazine-3,6-dione (salts)
succinic acid mono-N-dimethylhydrazide (salts)
(2-chloroethyl)-trimethylammonium chloride
(2-methyl-4-phenylsulfonyl)-trifluoromethanesulfone anilide
1,1-dimethyl-4,6-diisopropyl-5-indanyl ethyl ketone
sodium chlorate
ammonium thiocyanate
calcium cyanamide
2-chloro-4-trifluoromethyl-3'-ethoxycarbonyl)-4'-nitrophenyl ether
1-(4-benzyloxyphenyl)-3-methyl-3-methoxyurea
2-[1-(2,5-dimethylphenyl)-ethylsulfonyl]-pyridine-N-oxide.

It may also be useful to apply the novel compounds alone or in admixture with other herbicides or crop protection agents, e.g., agents for combating pests or phytopathogenic fungi or bacteria. The compounds may also be mixed with solutions of mineral matters used to remedy nutritional or trace element deficiencies. To initiate the herbicidal action, wetting agents, spreader-stickers and non-phytotoxic oils and oil concentrates may be added.

The influence of various representatives of the compounds according to the invention on the growth of unwanted and crop plants is demonstrated in the following greenhouse experiments.

The seeds of the test plants (cf. Table 1) were sown shallow, and separately, according to species. In the case of *Cyperus esculentus*, pregerminated tubers were planted, and *Mentha piperita* was also vegetatively propagated by means of stolons. The latter were for this reason only subjected to postemergence treatment. For the preemergence treatment, the active ingredients were applied to the surface of the soil immediately after the seeds had been sown. The compounds were emulsified or suspended in water as vehicle, and sprayed through finely distributing nozzles. After the agents had been applied, the vessels were lightly sprinkler-irrigated to induce germination and growth and to activate the chemical agents. Transparent plastic covers were then placed on the vessels until the plants had taken root. The cover ensured uniform germination of the plants, insofar as this was not imparied by the chemicals, and prevented readily volatile substances from evaporating.

For the postemergence treatment, the plants were first grown in the vessels to a height of from 3 to 10 cm, depending on growth form, before being treated. No cover was placed on the vessels.

The pots were set up in the greenhouse—species from warmer areas at from 25° to 40° C., and species from moderate climates at 15° to 30° C. The experiments were run for from 3 to 5 weeks. During this period, the plants were tended and their reactions to the various treatments assessed. The following tables contain the compounds investigated, the application rates in kg/ha of active ingredient, and the plants used for the tests. The scale used for assessment was 0 to 100, 0 denoting no damage or normal emergence, and 100 denoting nonemergence or complete destruction of at least the visible plant parts.

The following tables demonstrate the selective herbicidal action of the compounds according to the invention, which is directed mainly against Cyperaceae and broadleaved unwanted plants; the compounds also exhibited a considerable effect on perennial species among the plants tested. In addition to gramineous crop plants, the agents are surprisingly tolerated by some broadleaved crop plants. The agents were applied both pre- and postemergence. A special application technique is to spray the active ingredients with the aid of spraying equipment in such a way that the leaves of sensitive crop plants are if possible not hit; the active ingredients reach the soil or unwanted plants growing below the crop plants (post-directed, lay-by treatment).

In view of the many application methods possible, the agents according to the invention, or mixtures containing them, may be used in addition to the crop plants listed in the tables in a large number of other crops for eliminating unwanted growth.

The following crop plants are given by way of example:

| Botanical name | Common name |
| --- | --- |
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. altissima | sugarbeets |
| *Beta vulgaris* spp. rapa | fodder beets |
| *Beta vulgaris* spp. esculenta | table beets, red beets |
| *Brassica napus* var. napus | rape |
| *Brassica napus* var. napobrassica | |
| *Brassica napus* var. rapa | turnips |
| *Brassica rapa* var. silvestris | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | |
| *Citrus sinensis* | orange trees |

-continued

| Botanical name | Common name |
|---|---|
| Coffea arabica (Coffea canephora, Coffea liberica) | coffee plants |
| Cucumis melo | melons |
| Cucumis sativus | cucumbers |
| Cynodon dactylon | Bermudagrass in turf and lawns |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Panicum miliaceum | |
| Phaseolus lunatus | limabeans |
| Phaseolus mungo | mungbeans |
| Phaseolus vulgaris | snapbeans, green beans, dry beans |
| Pennisetum glaucum | |
| Petroselinum crispum | parsley |
| spp. tuberosum | |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | |
| Ricinus communis | |
| Saccharum officinarum | sugar cane |
| Secale cereale | rye |
| Sesamum indicum | sesame |
| Solanum tuberosum | Irish potatoes |
| Sorghum bicolor (S. vulgare) | grain sorghum |
| Sorghum dochna | |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

TABLE 1

| Bontanical name | Abbreviation in tables | Common name |
|---|---|---|
| Arachys hypogaea | | peanuts (groundnuts) |

TABLE 1-continued

| Bontanical name | Abbreviation in tables | Common name |
|---|---|---|
| Centaurea cyanus | | cornflower |
| Cucumis sativum | | cucumber |
| Cyperus esculentus | Cyperus escul. | yellow nutsedge |
| Datura stramonium | | Jimsonweed |
| Euphorbia geniculata | | South American member of the spurge family |
| Gossypium hirsutum | | cotton |
| Mentha piperita | Mentha pip. | peppermint |
| Nicandra physaloides | | apple of Peru |
| Sinapis alba | | white mustard |
| Sorghum bicolor | | sorghum |
| Solanum nigrum | | black nightshade |
| Asclepias spp. | Asclep. spp. | milkweed |
| Chenopodium album | Chenop. alb. | lambsquarters |
| Cyperus iria | Cyper. iria | annual sedge species |
| Datura stramoniu | Datura stram. | jimsonweed |
| Matricaria spp. | Matric. spp. | chamomile |

TABLE 2

Selective removal of unwanted plants in cucumbers; postemergence treatment in the greenhouse Active ingredient $$\begin{array}{c} O \\ \parallel \\ N \diagup \diagdown N-C_3H_{7i} \\ \parallel \quad \quad \mid \\ \quad \quad SO_2 \\ N \diagdown \diagup N \\ (CH_3)_2 \quad \mid \\ H \end{array}$$

| Test plants | No. 12 | No. 139 | prior art |
|---|---|---|---|
| | Damage (%) at 1.0 kg/ha | | |
| Cucumis sativum | 5 | 0 | 60 |
| Centaurea cyanus | 90 | 95 | 80 |
| Nicandra physaloides | 80 | — | 100 |
| Sinapis alba | 69 | 94 | 99 |
| Solanum nigrum | 95 | 100 | 100 |

TABLE 3

Control of broadleaved weeds in groundnuts; postemergence treatment in the greenhouse $$\begin{array}{c} O \\ \parallel \\ N \diagup \diagdown N-C_3H_{7i} \\ \parallel \quad \quad \mid \\ \quad \quad SO_2 \\ (CH_3)_2N \diagdown \diagup N \\ \mid \\ H \end{array}$$

| Test plants | Active ingredients No. 61 | prior art |
|---|---|---|
| | Damage (%) at 2.0 kg/ha | |
| Arachys hypogaea | 5 | 30 |
| Centaurea cyanus | 95 | 90 |
| Chenopodium album | 98 | 70 |
| Euphorbia geniculata | 95 | 45 |
| Nicandra physaloides | 100 | 100 |

TABLE 4

Selective Control of weeds in crops;
postemergence application in the greenhouse Active ingredients No. 91 prior art:

(CH₃)₂N—C(=N—)—N(C=O)—N(C₃H₇i)—SO₂—N(H)— (cyclic)

| Test plants | No. 91 | prior art |
|---|---|---|
| | Damage (%) at 2.0 kg/ha | |
| Gossypium hirsutum | 10 | 45 |
| Sorghum bicolor | 0 | 60 |
| Centaurea cyanus | 90 | 90 |
| Datura stramonium | 100 | 100 |
| Nicandra physaloides | 100 | 100 |
| Sinapis alba | 100 | 100 |

TABLE 5

Control of perennial plants; pre- and postemergence treatment in the greenhouse

| | | Test plants and % damage | | |
|---|---|---|---|---|
| | | Pre-emergence | Postemergence | |
| Active ingredient | kg/ha | Cyperus escul. | Cyperus escul. | Mentha pip. |
| 7 | 2,0 | 89 | 64 | 75 |
| | 3,0 | — | 100 | 100 |
| 32 | 2,0 | 95 | 75 | 85 |

TABLE 6

Selective control of unwanted plants; postemergence treatment in the greenhouse

| | | Test plants and % damage | | | | | | | |
|---|---|---|---|---|---|---|---|---|---|
| Active ingredient | kg/ha | Gossyp. hirs. | Oryza sat. | Tritic. aest. | Asclep. spp. | Chenop. alb. | Cyper. iria | Datura stram. | Matric. spp. |
| 64 | 1.0 | 0 | 0 | 0 | 70 | 100 | 90 | 90 | 100 |

0 = no damage
100 = plants destroyed

We claim:
1. A 5,6-dihydro-1,2,4,6-thiatriazin-5-one-1,1-dioxide of the formula

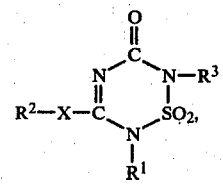

I where
R¹ is hydrogen, a metal atom or an unsubstituted or substituted ammonium radical,
R² is saturated or unsaturated straight-chain aliphatic radical of up to 10 carbon atoms, a cycloaliphatic radical of 3 to 7 carbon atoms, a branched saturated or unsaturated aliphatic radical of 3 to 10 carbon atoms, a halogen-, alkoxy- or alkylmercapto-substituted aliphatic radical of 2 to 10 carbon atoms, tetrahydrofuryl substituted methyl, a cycloalkoxy-substituted aliphatic radical of 4 to 10 carbon atoms, unsubstituted or halogen-substituted benzyl or phenyl, halophenyl or alkylphenyl of a total of up to 10 carbon atoms,
R³ is hydrogen, a straight-chain aliphatic radical of up to 10 carbon atoms, a cycloaliphatic radical of 3 to 7 carbon atoms, a branched aliphatic radical of 3 to 10 carbon atoms, haloalkyl, or alkoxyalkyl of 2 to 10 carbon atoms and
X is oxygen and may also be sulfur if R² is unsubstituted or halogen-substituted benzyl.
2. A 5,6-dihydro-1,2,4,6-thiatriazin-5-one-1,1-dioxide selected from the group consisting of 6-methyl-3-methoxy-5,6-dihydro-1,2,4,6-thiatriazin-5-one-1,1-dioxide, 6-methyl-3-ethoxy-5,6-dihydro-1,2,4,6-thiatriazin-5-one-1,1-dioxide, 6-ethyl-3-methoxy-5,6-dihydro-1,2,4,6-thiatriazin-5-one-1,1-dioxide and 6-ethyl-3-ethoxy-5,6-dihydro-1,2,4,6-thiatriazin-5-one-1,1-dioxide.

* * * * *